(12) United States Patent
Koponen et al.

(10) Patent No.: US 10,912,949 B2
(45) Date of Patent: Feb. 9, 2021

(54) MULTI-CRITERIA OPTIMIZATION TOOLS INCLUDING TIME-BASED CRITERIA FOR RADIATION THERAPY

(71) Applicants:Varian Medical Systems, Inc., Palo Alto, CA (US); Varian Medical Systems International AG, Cham (CH); Varian Medical Systems Particle Therapy GmbH, Troisdorf (DE)

(72) Inventors: Timo Koponen, Espoo (FI); Perttu Niemela, Espoo (FI); Markus Bach, Overath (DE); Jan Timmer, Los Altos, CA (US); Christel Smith, Santa Barbara, CA (US)

(73) Assignees: Varian Medical Systems, Inc., Palo Alto, CA (US); Varian Medical Systems International AG, Cham (CH)

( * ) Notice: Subject to any disclaimer, the term of this patent is extended or adjusted under 35 U.S.C. 154(b) by 210 days.

(21) Appl. No.: 16/147,104

(22) Filed: Sep. 28, 2018

(65) Prior Publication Data

US 2020/0101317 A1 Apr. 2, 2020

(51) Int. Cl.
*A61N 5/10* (2006.01)
(52) U.S. Cl.
CPC .......... *A61N 5/103* (2013.01); *A61N 5/1037* (2013.01); *A61N 5/1081* (2013.01); *A61N 2005/1087* (2013.01)

(58) Field of Classification Search
CPC ..... A61N 5/103; A61N 5/1037; A61N 5/1081
USPC ........................................................ 600/1-8
See application file for complete search history.

(56) References Cited

U.S. PATENT DOCUMENTS

| 8,961,382 B2 | 2/2015 | Nord et al. |
| 2009/0321665 A1 | 12/2009 | Timmer et al. |
| 2013/0187062 A1 | 7/2013 | Nord et al. |
| 2016/0279447 A1 | 9/2016 | Timmer et al. |
| 2017/0266462 A1 | 9/2017 | Kesti-Helia et al. |
| 2018/0021595 A1 | 1/2018 | Kesti-Helia et al. |
| 2018/0165423 A1 | 6/2018 | Kuusela et al. |

FOREIGN PATENT DOCUMENTS

| EP | 3530319 | 8/2019 |
| WO | 2015090457 | 6/2015 |
| WO | 2016144914 | 9/2016 |

*Primary Examiner* — John P Lacyk (57) ABSTRACT

Multi-criteria optimization of radiation therapy tools for receiving a plurality of criteria including one or more sets of competing objectives. The competing objective can include delivery time criteria, fractionation criteria or similar time-based criteria. One or more radiation therapy plans can be determined based on a multi-criteria optimization of the plurality of criteria for the radiation therapy treatment. The one or more optimized radiation therapy plans can be output for consideration by one or more members of a radiation oncology team.

20 Claims, 9 Drawing Sheets

MULTI-CRITERIA OPTIMIZATION TOOLS INCLUDING TIME-BASED CRITERIA FOR RADIATION THERAPY

BACKGROUND OF THE INVENTION

Computing systems have made significant contributions toward the advancement of modern society and are utilized in a number of applications to achieve advantageous results. Numerous devices, such as desktop personal computers (PCs), laptop PCs, tablet PCs, netbooks, smart phones, servers, and the like have facilitated increased productivity and reduced costs in communicating and analyzing data in most areas of entertainment, education, business, and science. In the health care industry, computing devices can be utilized in the diagnosis, planning and treatment of tumors, cancers and the like.

In oncology, Radiation Therapy (RT) utilizes ionizing radiation to control or kill tumors, or prevent the recurrence of tumors after other medical procedures. In cancerous tumors, ionizing radiation can damage the DNA of cancerous tissue leading to cellular death. To spare normal tissue, shaped radiation beams can be aimed from several angles to intersect at the tumor, providing a much larger absorbed dose in the tumor than in the surrounding health tissue. Common types of radiation therapy include radiotherapy and radiosurgery. Radiotherapy is typically delivered in relatively smaller doses, five days a week for four to six weeks. Radiosurgery is typically delivered in relatively larger doses in one to five treatment. The number and frequency of treatments is typically referred to as the fractionation schedule.

Computing systems are utilized to develop radiation therapy treatment plans specific to each patient. The computing device is typically utilized to develop a treatment plan including the number of beams, the radiation dosage, and the number of sessions to deliver the full treatment. There is a continuing need for radiation therapy treatment tools for developing radiation therapy plans and administering the radiation therapy treatment according to the plan.

SUMMARY OF THE INVENTION

The present technology may best be understood by referring to the following description and accompanying drawings that are used to illustrate embodiments of the present technology directed toward multi-criteria optimization of radiation therapy.

In one embodiment, a radiation therapy treatment planning method can include receiving a plurality of criteria for a radiation therapy treatment. The plurality of criteria can include one or more sets of competing objectives. The competing objectives can include time-based criteria such as delivery time criteria, fractionation criteria or the combination thereof. Additional criteria can also include the modality of the treatment, target volume of the tissue, number of beams, radiation dosage, monitor unit, organ-at-risk, normal tissue complication probability, and the like. One or more radiation therapy plans can be determined based on a multi-criteria optimization of the criteria. The one or more optimized radiation therapy plans can be output for consideration by one or more members of a radiation oncology team. In addition, the method can include receiving one or more revised criteria. One or more revised radiation therapy plans can be determined based on the multi-criteria optimization of the revised criteria. The revised radiation therapy plans can also be output to the team members for further consideration.

In another embodiment, a plurality of criteria parameter values for a first type of radiation therapy treatment can be received. A plurality of criteria for a second type of radiation therapy treatment can also be received. Again, the plurality of criteria can include one or more sets of competing objective. The competing objectives can include time-based criteria such as delivery time criteria, fractionation criteria or the combination thereof. One or more radiation therapy plans can be determined based on a multi-criteria optimization of the plurality of criteria for the second type of radiation therapy treatment constrained by the one or more criteria parameter values for the second type of radiation therapy treatment. The one or more optimized radiation therapy plans of the second type can be output for consideration by one or more members of a radiation oncology team. In addition, the method can include receiving revised criteria for the second type of radiation therapy treatment. One or more revised radiation therapy plans can be determined based on the multi-criteria optimization of the revised criteria. The revised radiation therapy plans can also be output to one or more team members for further consideration.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which.

DETAILED DESCRIPTION OF THE INVENTION

Reference will now be made in detail to the embodiments of the present technology, examples of which are illustrated in the accompanying drawings. While the present technology will be described in conjunction with these embodiments, it will be understood that they are not intended to limit the invention to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that all of these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

In this application, the use of the disjunctive is intended to include the conjunctive. The use of definite or indefinite articles is not intended to indicate cardinality. In particular, a reference to "the" object or "a" object is intended to denote also one of a possible plurality of such objects. It is also to be understood that the phraseology and terminology used herein is for the purpose of description and should not be regarded as limiting.

Figure 1:
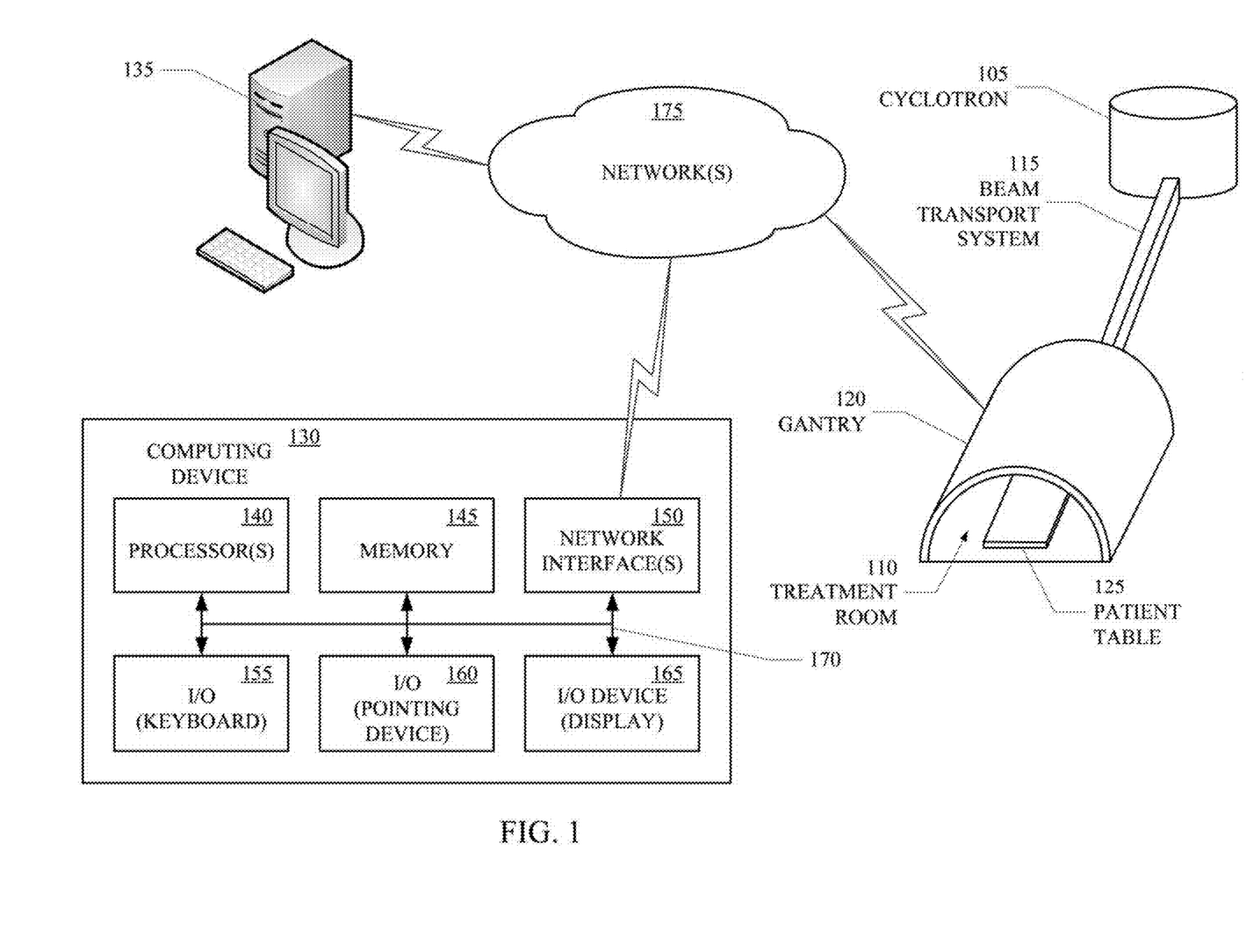
FIG. 1 shows an exemplary radiation therapy treatment system, in accordance with aspects of the present technology.

Referring to FIG. 1, an exemplary radiation therapy treatment system, in accordance with aspects of the present technology, is shown. The system can include one or more radiation therapy treatment devices 105-125 and one or more computing devices 130, 135 coupled to the radiation treatment devices 105-125. The term Radiation Therapy (RT) will be used herein after to refer to radiotherapy, radiosurgery and similar oncology methods and devices. In a proton beam radiation therapy example, the radiation therapy treatment device 105-125 can include a cyclotron 105, and one or more treatment rooms 110 coupled to the cyclotron 105 by one or more beam transport systems 115. Each treatment room 110 can include a gantry 120 and a patient table 125. The cyclotron 105 uses electromagnetic waves to accelerate one or more proton beams. The beam transport system 115 can be configured to focus and shape the proton beams and guide them to the gantries 120 in the one or more treatment rooms 110. The gantry 120 can rotate about the patient to deliver proton beams at any angle while minimizing the need to reposition the patient. The treatment room 110 can include a patient table 125 about which the gantry 120 is disposed. The table 125 can include a sophisticated patient positioning system that moves in one or more directions to position patients. Proton therapy can more precisely localize the radiation dosage compared to other types of external beam radiotherapy. In one implementation, the proton therapy can be Image-Guided Proton Therapy (IGPT), which is enabled by high resolution digital imaging systems providing stereoscopic imaging in an orthogonal arrangement. In another implementation, Intensity-Modulated Proton Therapy (IMPT) can be a highly precise type of radiation therapy using an intensity modulated proton beam. The above described exemplary proton beam radiation therapy treatment device is not intended to limit aspects of the present technology. Other exemplary radiation therapy treatment devices can include photon beam radiation therapy treatment devices, electron beam radiation therapy treatment devices, or the like.

One or more of the computing devices 130, 135 can be configured to control the operation of the cyclotron 105, the beam transport systems 115, the gantries 120 and/or patient tables 125. One or more of the computing devices 130, 135 can also be configured to generate patient radiation therapy treatment plans. The one or more computing devices 130, 135 can include one or more processors 140, one or more memories 145, one or more network interface 155, and one or more input/output devices such as keyboards, pointing devices, displays and/or the like, coupled together by one or more busses 170. The one or more computing devices 130, 135 can be any type of computing device, including but not limited to desktop Personal Computers (PCs), laptop PCs, server computer, virtual machine, cloud computing platform, or the like. The one or more computing devices 130, 135 can be coupled directly to the one or more radiation therapy treatment devices 105-125 or can be coupled through one or more networks 175, including Local Area Networks (LAN), Wide Area Networks (WAN), the Internet or the like. Alternatively, one or more of the computing devices 130, 135 can be integral to the radiation therapy treatment devices 105-125.

In the conventional art a radiation therapy treatment plan may typically be optimized solely for dose-based constraints and objectives. However, many other factors that play a dominant role in the patient's treatment and subsequent outcome may not be addressed in conventional treatment planning processes. Other important factors can include treatment modality, delivery time, fractionation schedule, toxicity probabilities, motion management, and the economic tradeoffs thereof. Treatment modality refers to the type of radiation therapy, such as photon vs proton. Delivery time refers to the time length of each radiation dosage. Fractionation refers to the number of treatments that the total radiation dosage is delivered in. Toxicity probabilities refers to the likelihood of an adverse side effect given the amount of radiation that normal tissue and organs at risk am subject to while the panned target volume of the target tumor is being treated. Motion management refers to controlling or compensating for the movement of the target tumor by reducing external movement of the patient during treatment and/or internal movement within the patient due to such functions as breathing, the bladder filling and the like during treatment. Conventionally, a few best practices guide the decision that influence the above noted key factors. The decisions are often made through the physician's preference and background, or the standard operating procedures of the given clinic, without guidance tools.

In proton radiation therapy, for example, the delivery time can be determined by factors such as the number of energy layers, monitor units per scan spot or line, and their distribution. For instance, limiting the minimum allowed dose per spot or line delivered can speed up the beam, but it is likely to simultaneously reduce the quality of the dose distribution. In general, there is a tradeoff between the clinical quality of the treatment plan and the delivery time.

Figure 2:
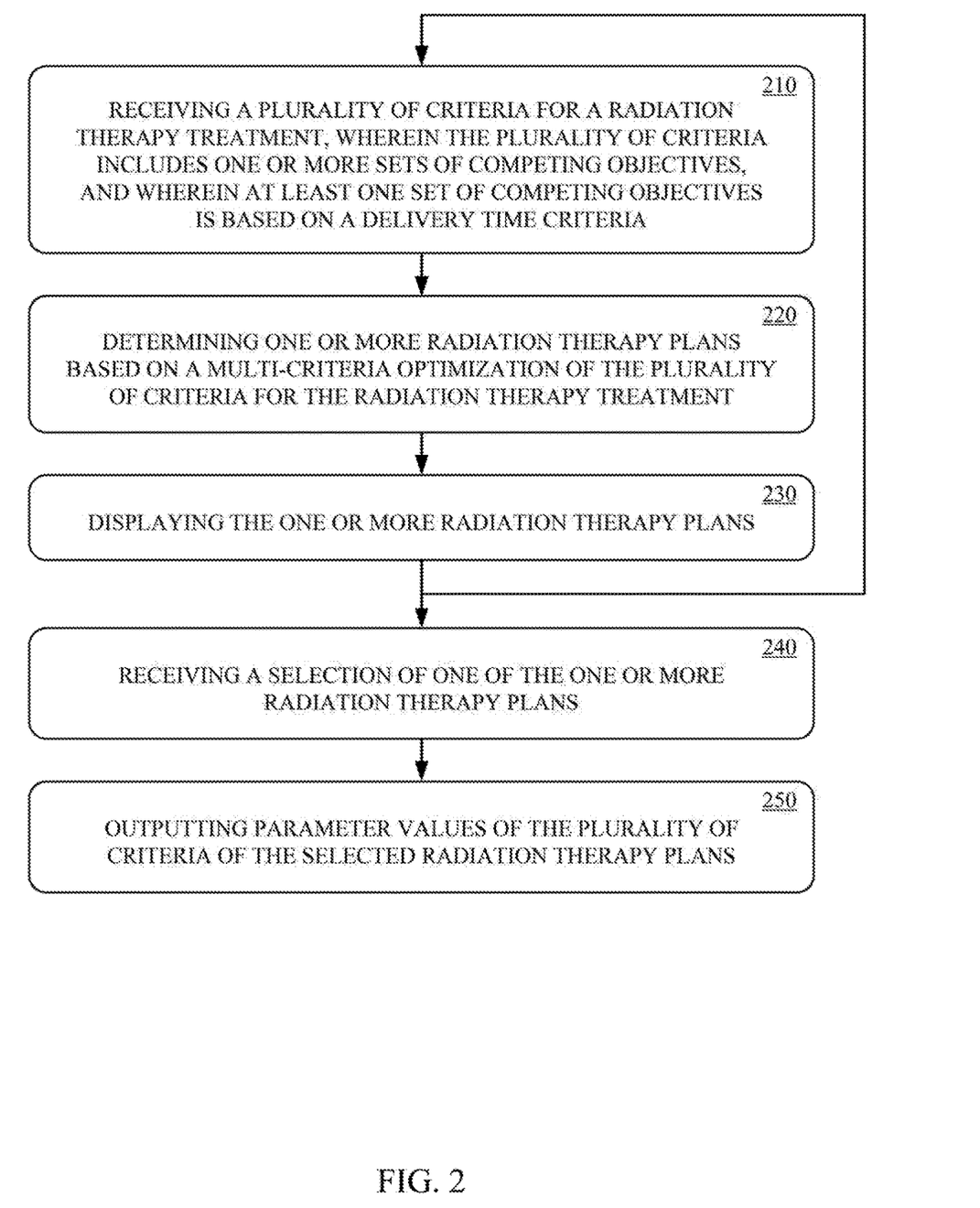
FIG. 2 shows a radiation therapy treatment planning method, in accordance with aspects of the present technology.

Referring now to FIG. 2, a radiation therapy treatment planning method, in accordance with aspects of the present technology, is shown. The method may be implemented as computing device-executable instructions (e.g., computer program) that are stored in computing device-readable media (e.g., computer memory) and executed by a computing device (e.g., processor). The method can include receiving a plurality of criteria for a radiation therapy treatment, at 210. The criteria can include one or more constraints, objectives, and the like. The criteria can be received by a computing device 130 from one or more individuals of a Radiation Oncology (RO) team. In one implementation, a radiation oncology team, that can include one or more physician and dosimetrists, can begin with a modality preparation phase. The radiation oncology team can, for instance, consider potential options including a best in class (e.g., quality) photon plan, a best in class proton plan, a fastest hypo-fractionated proton plan substantially equivalent in quality to the best in class photon plan, and/or the like. The radiation oncology team can enter criteria of one or more of the options via a keyboard, pointing device (e.g., mouse) and/or touchscreen of the computing device.

The criteria can include one or more sets of competing objectives, wherein at least one set of competing objectives is based on a delivery time criteria. For example, the radiation oncology team can also identify one or more mechanisms that affect the delivery time of the treatment options. For instance, in Intensity-Modulated Proton Therapy (IMPT) optimization-a smoothing objective or minimum Monitor Unit (MU) constraint can be identified to control the variations in spot monitor units within a single energy layer. Some other parameters that affect treatment time, can include the number of energy layers, the number of beams, the beam direction, and the like.

At 220, one or more radiation therapy plans based on a Multi-Criteria Optimization (MCO) of the plurality of criteria can be determined. The multi-criteria optimization can be based on a no preference multi-criteria optimization, a priori multi-criteria optimization, a posteriori multi-criteria optimization, an interactive multi-criteria optimization or the like. In one implementation, the computing device 130 can be configured to perform a multi-criteria optimization based on the plurality of received criteria. For example, a solution set of Pareto optimal plans can be created, wherein the unique combinations of dose and delivery time can be explored. The values, priorities and the like of the competing objectives can be varied in addition to the dose-based objectives in order to create multiple candidate plans and to adequately sample the available space between different tradeoffs. In one implementation, the dose to target volume as a variable can be optimized (e.g., maximized) as opposed to being prescribed by the physician. In addition, criteria such as economic parameters can also be utilized in the optimization for the treatment planning process.

Figure 3:
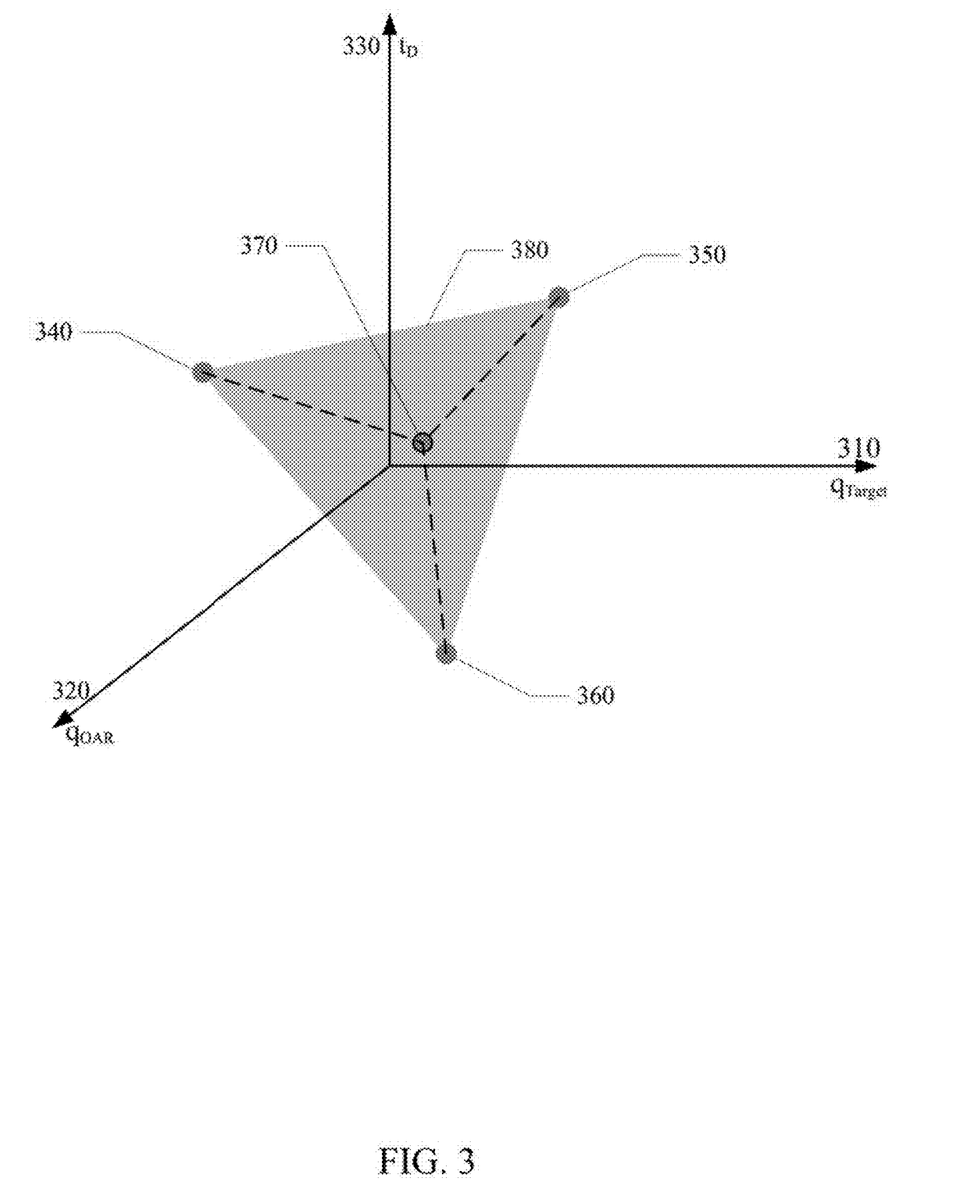
FIG. 3 illustrates an exemplary three-dimensional multi-criteria optimization search space, in accordance with aspect of the present technology.

Referring now to FIG. 3, an exemplary three-dimensional multi-criteria optimization search space, in accordance with aspect of the present technology, is shown. In the three-dimensional multi-criteria search space, two dimensions are quality metrics related to dose, the dose quality at the target 310 and the dose quality for organs-at-risk 320, and the third dimension is the delivery time 330. The dots 340-370 represent candidate plans that can be created by the automatic plan generation process and the shaded area 380 represent the Pareto optimal search space available during the interactive phase of the multi-criteria optimization search.

Referring again to FIG. 2, the one or more radiation therapy plans determined based on the multi-criteria optimization can be displayed, at 230. In one implementation, the one or more radiation therapy plans can be output on a display 165 by the computing device 130. The one or more radiation therapy plans can be displayed in one or more Graphical User Interfaces (GUIs) to one or more decision makers. In addition, the one or more radiation therapy plans can be stored in one or more computing device accessible data structures in the memory 145 of the computing device, in network attached storage, in cloud storage, or the like.

The processes at 210-230 can be iteratively repeated any number of times. The planner is therefore, presented with the tools to compare the plans for dose coverage and treatment time, and estimate results base on the plans for other possible sets of radiation therapy treatment criteria. The processes at 210-230 can be repeated to determine a radiation therapy plan in each iterative cycle. In other implementations, multiple radiation therapy plans can be determined in each iterative cycle. Subsequent iterative cycles can also be used to determine new plans based on variations in treatment plans determined in previous cycles or linear combinations of multiple treatment plans determined in previous cycles.

In one implementation, an estimate of the delivery time can be computed for each candidate plan. The delivery time can then be used as an additional quality metric, which together with a set of selected dose-related quality metrics can define the position of the plan in the multi-dimensional tradeoff space. Based on the computed quality metric values, the iterative multi-criteria optimization can be performed. In the iterative phase, the user can have control of each selected quality metric, including the treatment time, and can therefore quickly explore Pareto optimal tradeoffs between the metrics.

At 240, a selection of one or more of the determined radiation therapy plans can be received. In one implementation, the computing device 130 can receive a selection of a given radiation therapy plan by the radiation oncology team. At 250, parameter values of the plurality of criteria of the one or more selected radiation therapy plans can be output. In one implementation, the computing device 130 can output the parameter values of the selected radiation therapy plan for storage in a computing device executable data structure. In another implementation, the parameter values of the selected radiation therapy plan can be output to the radiation therapy treatment device 105-125 for controlling operation thereof.

Accordingly, the workflow of the radiation therapy treatment planning method can include two phases. In the first phase, a plurality of candidate treatment plans can be created by a multi-criteria optimization wherein competing objects including the delivery time are utilized. In the second phase, the planner can interactively explore the space spanned by the candidate plans, and their linear combinations, to select a result that will either be used directly or converted to a deliverable treatment plan.

Another challenge is that a given radiation therapy modality can be more expensive than another. For example, proton therapy is typically more expensive per fraction than photon therapy. Insurance companies may be reluctant to pay more per fraction for dosimetric quality improvements. This can make it challenging for a proton therapy center, for example, to operate profitably as they typically prescribe based off standard and costly fractionation schedules.

Figure 4:
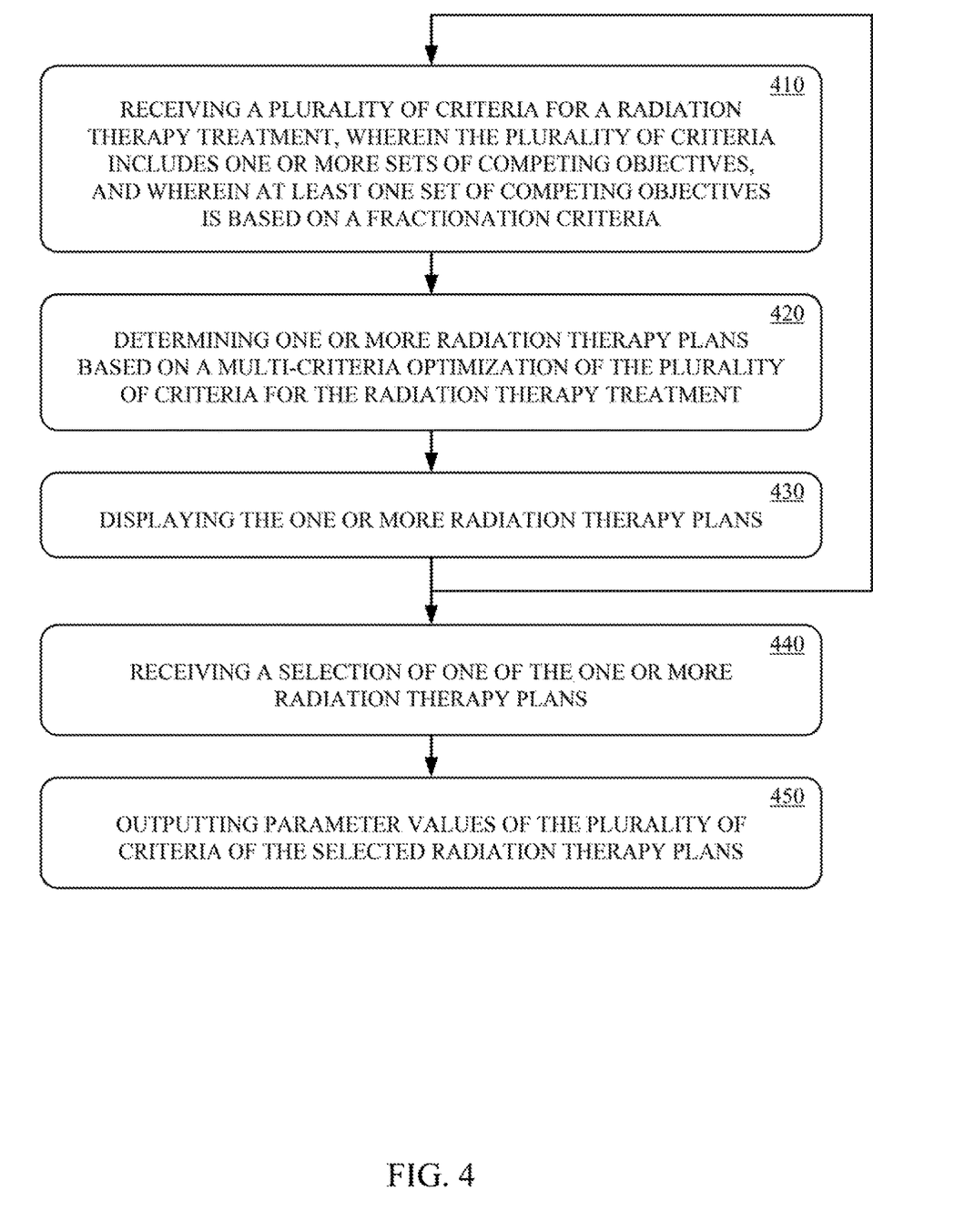
FIG. 4 shows a radiation therapy treatment planning method, in accordance with aspects of the present technology.

Referring now to FIG. 4, a radiation therapy treatment planning method, in accordance with aspects of the present technology, is shown. Again, the method may be implemented as computing device-executable instructions (e.g., computer program) that are stored in computing device-readable media (e.g., computer memory) and executed by a computing device (e.g., processor). The method can include receiving a plurality of criteria for a radiation therapy treatment, at 410. The criteria can include one or more constraints, objectives and the like, wherein at least one set of competing objectives is based on a fractionation criteria. For example, the radiation oncology team can also identify one or more mechanism that affect the number of treatments that the total radiation dosage is delivered in. The criteria can be received by a computing device 130 from one or more individuals of the radiation oncology team.

At 420, one or more radiation therapy plans based on a multi-criteria optimization of the plurality of criteria can be determined. In one implementation, the computing device 130 can be configured to perform a multi-criteria optimization based on the plurality of received criteria. For example, a solution set of Pareto optimal plans can be created, wherein the unique combinations of dose and fractionation can be explored. The values, priorities and the like of the competing objectives can be varied in addition to the fractionation-based objectives in order to create multiple candidate plans and to adequately sample the available space between different tradeoffs.

At 430, the one or more radiation therapy plans determined based on the multi-criteria optimization can be displayed. In one implementation, the one or more radiation therapy plans can be output on a display 165 by the computing device 130. The one or more radiation therapy plans can be displayed in one or more Graphical User Interfaces (GUIs) to one or more decision makers. In addition, the one or more radiation therapy plans can be stored in one or more computing device accessible data structures in the memory 145 of the computing device, in network attached storage, in cloud storage, or the like.

The processes at 410-430 can be iteratively repeated any number of times. The planner is therefore, presented with the tools to compare the plans for dose coverage and fractionation, and estimate results based on the plans for other possible sets of radiation therapy treatment criteria. The processes at 410-430 can be repeated to determine a radiation therapy plan in each iterative cycle. In other implementations, multiple radiation therapy plans can be determined in each iterative cycle. Subsequent iterative cycles can also be used to determine new plans based on variations in treatment plans determined in previous cycles or linear combinations of multiple treatment plans determined in previous cycles.

In one implementation, an estimate of the fractionation schedule can be computed for each candidate plan. The given fractionation can then be used as an additional quality metric, which together with a set of selected fractionation-related quality metrics can define the position of the plan in the multi-dimensional tradeoff space. Based on the computed quality metric values, the iterative multi-criteria optimization can be performed. In the iterative phase, the user can have control of each selected quality metric, including the fractionation, and can therefore quickly explore Pareto optimal tradeoffs between the metrics. For example, the planner can lock the normal tissue complication probability for a proton therapy plan and then reduce the number of fractions for proton plan, wherein a per fraction dose is increased. A Pareto optimal proton treatment plan can result in substantially reduced treatment costs due to the use of fewer fractions with substantially the same toxicity likelihood.

Figure 5:
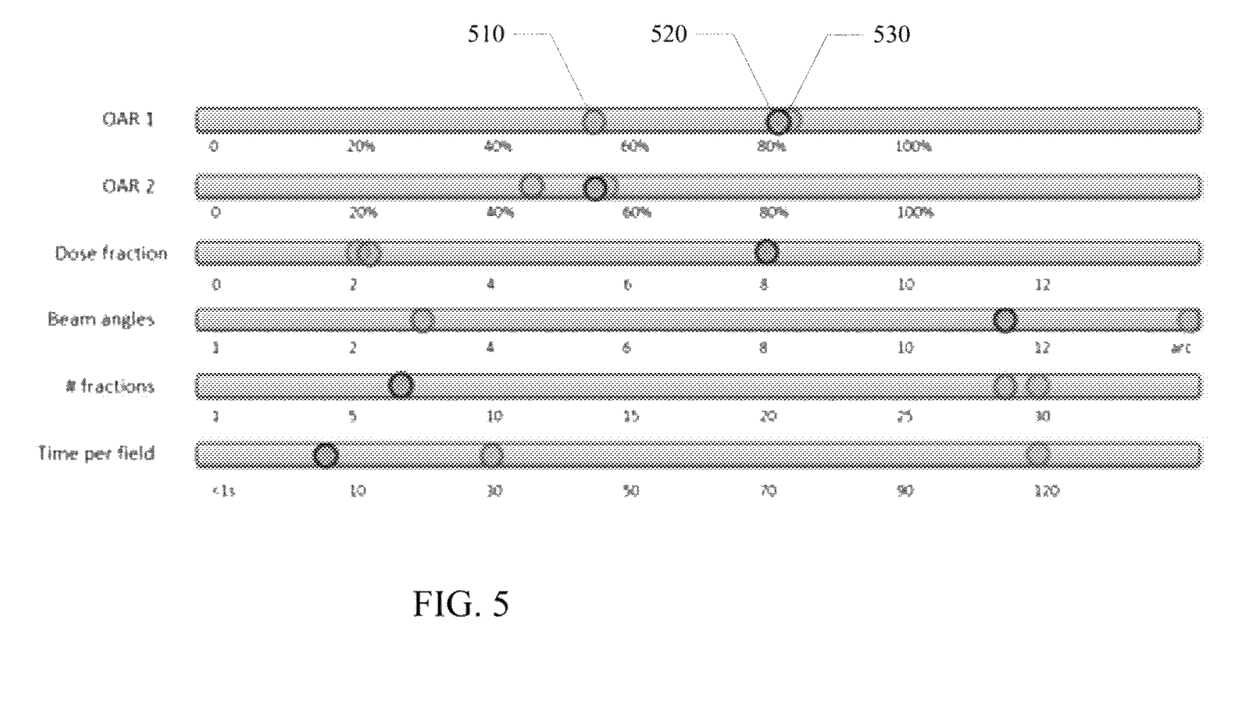
FIG. 5 illustrates an exemplary graphical user interface for displaying determined multi-criteria optimization radiation treatment plans, in accordance with aspects of the present technology.
Figure 6:
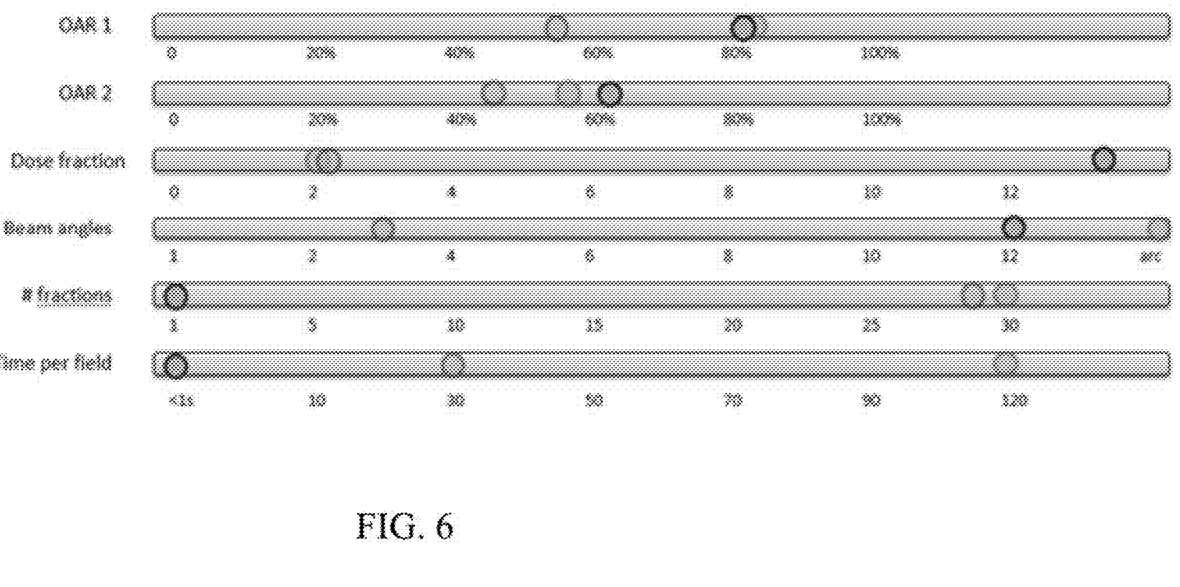
FIG. 6 illustrates an exemplary graphical user interface for displaying determined multi-criteria optimization radiation treatment plans, in accordance with aspects of the present technology.
Figure 7:
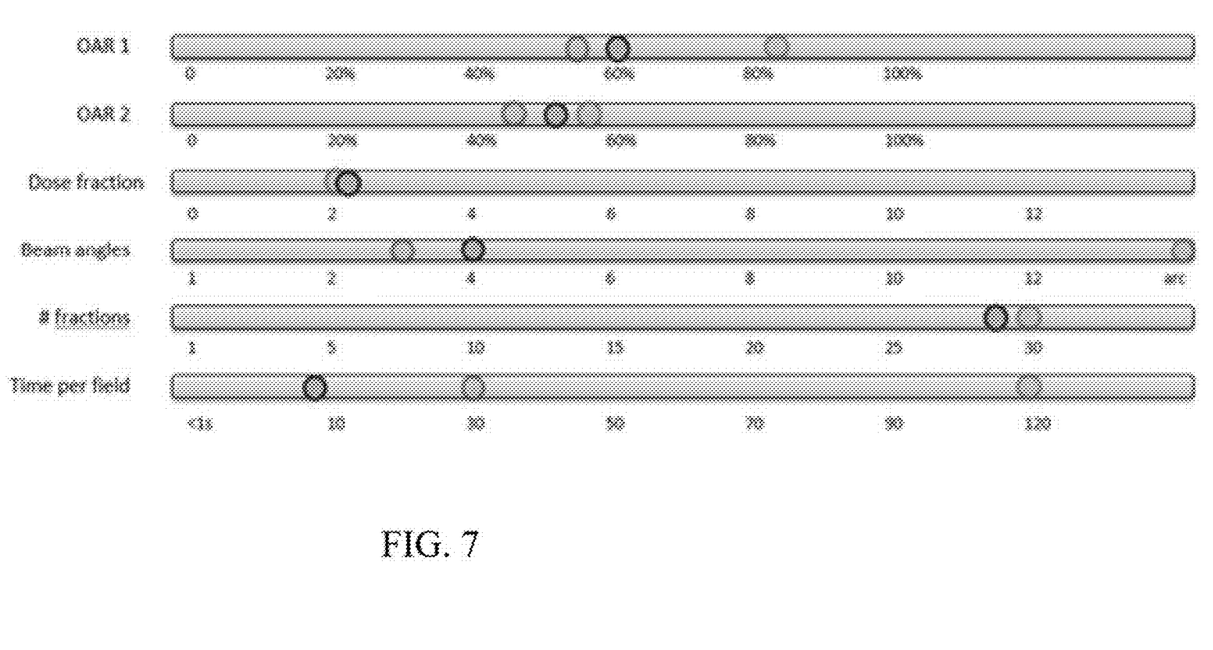
FIG. 7 illustrates an exemplary graphical user interface for displaying determined multi-criteria optimization radiation treatment plans, in accordance with aspects of the present technology.

Referring now to FIG. 5, an exemplary graphical user interface for displaying determined multi-criteria optimization radiation treatment plans, in accordance with aspects of the present technology, is shown. As illustrate, criteria of one or more competing objects for three candidate radiation therapy plans 510-530 are presented in a graphical user interface. The criteria can include a percentage of maximum allowable dosage from a first and second Organ-At-Risk (OAR1, OAR2), a dose fraction, a beam angle arc, a number of fractions, and a delivery time per field. The radiation treatment plans can be optimized for a minimum number of fractions. The radiation oncology team can visual compare the tradeoffs between the three optimized treatment plans 510-530. Referring now to FIG. 6, another set of determined multi-criteria optimized radiation treatment plans, in accordance with aspects of the present technology, is shown. The illustrated treatment plans can include a flash plan, which delivers the dose in a single session (the number of fractions equal one). Referring now to FIG. 7, yet another set of determined multi-criteria optimized radiation treatment plans, in accordance with aspects of the present technology, is shown. The illustrate treatment plans can be optimized for motion management.

Referring again to FIG. 4, a selection of one or more of the determined radiation therapy plans can be received, at 440. In one implementation, the computing device 130 can receive a selection of a given radiation therapy plan by the radiation oncology team. At 450, parameter values of the plurality of criteria of the one or more selected radiation therapy plans can be output. In one implementation, the computing device 130 can output the parameter values of the selected radiation therapy plan for storage in a computing device executable data structure. In another implementation, the parameter values of the selected radiation therapy plan can be output to the radiation therapy treatment device 105-125 for controlling operation thereof.

Accordingly, the workflow of the radiation therapy treatment planning method can include two phases. In the first phase, a plurality of candidate treatment plans can be created by a multi-criteria optimization wherein competing objects including fractionation are utilized. In the second phase, the planner can interactively explore the space spanned by the candidate plans, and their linear combinations, to select a result that will either be used directly or converted to a deliverable treatment plan.

Figure 8:
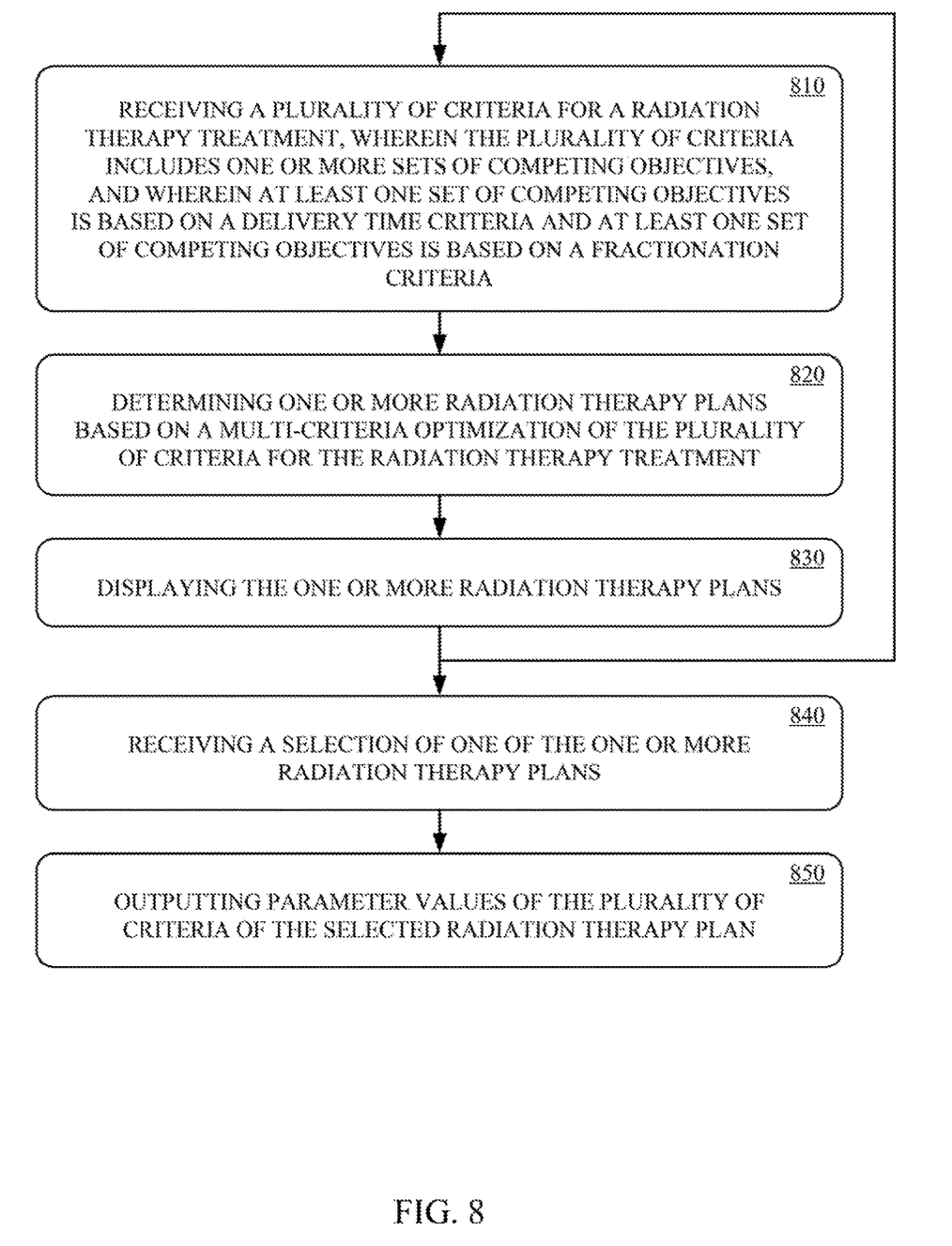
FIG. 8 shows a radiation therapy treatment planning method, in accordance with aspects of the present technology.

Referring now to FIG. 8, a radiation therapy treatment planning method, in accordance with aspects of the present technology, is shown. Again, the method may be implemented as computing device-executable instructions (e.g., computer program) that are stored in computing device-readable media (e.g., computer memory) and executed by a computing device (e.g., processor). The method can include receiving a plurality of criteria for a radiation therapy treatment, at 810. The criteria can include one or more constraints, objectives and the like, wherein at least one set of competing objectives is based on a delivery time criteria and at least one set of competing objectives is based on a fractionation criteria. For example, the radiation oncology team can identify one or more mechanisms that affect the delivery time of the treatment options and one or more mechanisms that affect the number of treatments that the total radiation dosage is delivered in. The radiation oncology team can enter criteria of one or more of the options via a keyboard 155, pointing device (e.g., mouse) 160 and/or touchscreen display 165 of the computing device 130.

At 820, one or more radiation therapy plans based on a multi-criteria optimization of the plurality of criteria can be determined. In one implementation, the computing device 130 can be configured to perform a multi-criteria optimization based on the plurality of received criteria. For example, a solution set of Pareto optimal plans can be created, wherein the unique combinations of dose, delivery time and fractionation can be explored. The values, priorities and the like of the competing objectives can be varied in addition to the delivery time-based objectives and fractionation-based objectives in order to create multiple candidate plans and to adequately sample the available space between different tradeoffs.

At 830, the one or more radiation therapy plans determined based on the multi-criteria optimization can be displayed. In one implementation, the one or more radiation therapy plans can be output on a display 165 by the computing device 130. The one or more radiation therapy plans can be displayed in one or more Graphical User Interfaces (GUIs) to one or more decision makers. In addition, the one or more radiation therapy plans can be stored in one or more computing device accessible data structures in the memory 145 of the computing device, in network attached storage, in cloud storage, or the like.

The processes at 810-830 can be iteratively repeated any number of times. The planner is therefore, presented with the tools to compare the plans for dose coverage, delivery time and fractionation, and can estimate results base on the plans for other possible sets of radiation therapy treatment criteria. The processes at 810-830 can be repeated to determine a radiation therapy plan in each iterative cycle. In other implementations, multiple radiation therapy plans can be determined in each iterative cycle. Subsequent iterative cycles can also be used to determine new plans based on variations in treatment plans determined in previous cycles or linear combinations of multiple treatment plans determined in previous cycles.

In one implementation, an estimate of the delivery time and fractionation schedule can be computed for each candidate plan. The given delivery time and fractionation can then be used as an additional quality metric, which together with a set of selected delivery time-related metrics and fractionation-related quality metrics can define the position of the plan in the multi-dimensional tradeoff space. Based on the computed quality metric values, the iterative multi-criteria optimization can be performed. In the iterative phase, the user can have control of each selected quality metric, including the delivery time and the fractionation, and can therefore quickly explore Pareto optimal tradeoffs between the metrics.

At 840, a selection of one or more of the determined radiation therapy plans can be received. In one implementation, the computing device 130 can receive a selection of a given radiation therapy plan by the radiation oncology team. At 850, parameter values of the criteria of the selected radiation therapy plan can be output. In one implementation, the computing device 130 can output the parameter values of the selected radiation therapy plan for storage in a computing device executable data structure. In another implementation, the parameter values of the selected radiation therapy plan can be output to the radiation therapy treatment device 105-125 for controlling operation thereof.

Figure 9:
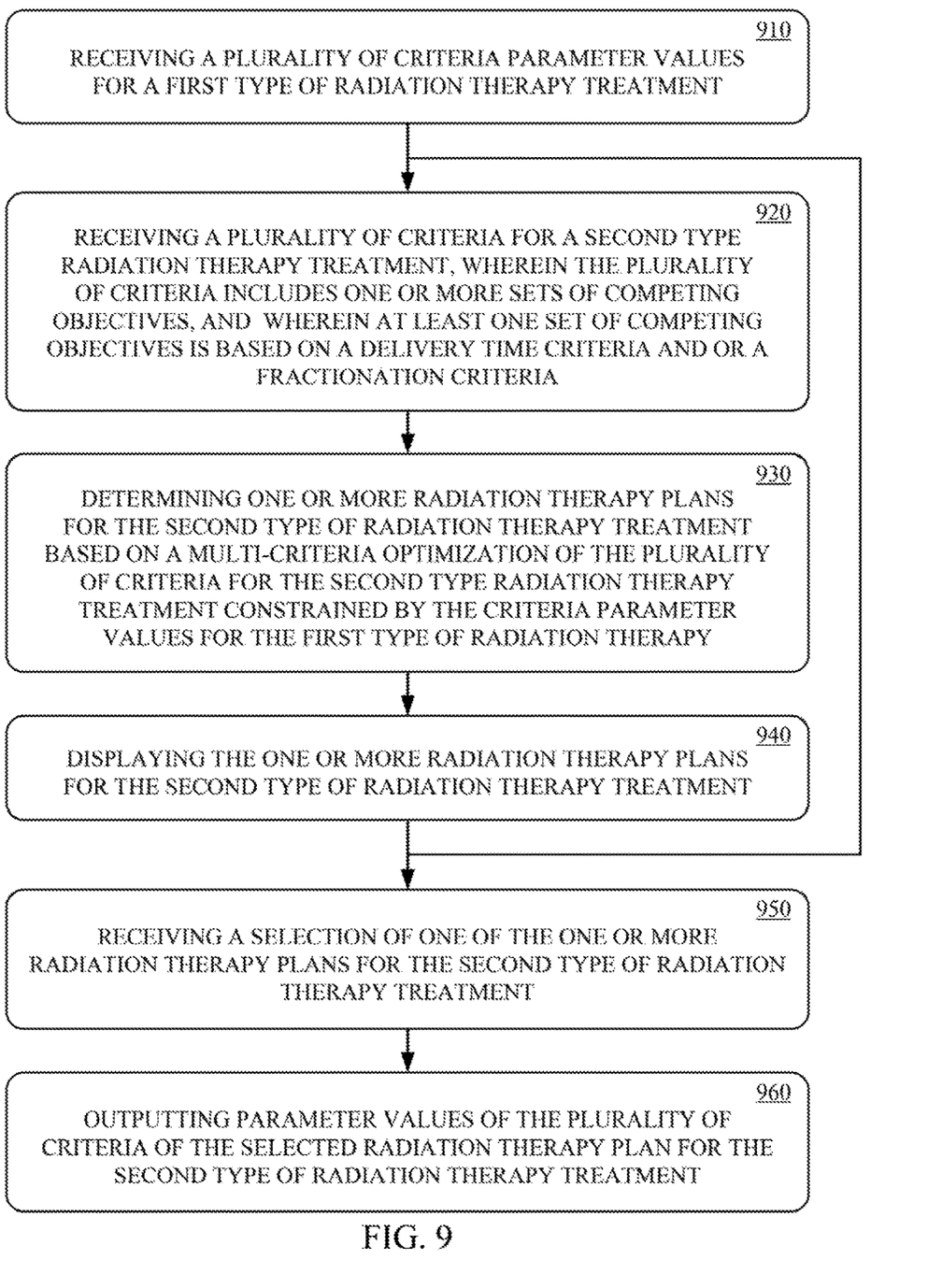
FIG. 9 shows a radiation therapy treatment planning method, in accordance with aspects of the present technology.

Referring now to FIG. 9, a radiation therapy treatment planning method, in accordance with aspects of the present technology, is shown. The method may be implemented as computing device-executable instructions (e.g., computer program) that are stored in computing device-readable media (e.g., computer memory) and executed by a computing device (e.g., processor). The method can include receiving parameter values of a plurality of criteria for a first type of radiation therapy treatment, at 910. The criteria for a first type of radiation therapy treatment can be received from a radiation therapy treatment planning tool. One or more of the criteria for the first type of radiation therapy treatment can also be entered by a radiation oncology team. At 920, a plurality of criteria for a second type of radiation therapy treatment can also be received. The criteria for the second type of radiation therapy treatment can include one or more constraints, objectives, and the like. The criteria for the second type of radiation therapy treatment can include one or more sets of competing objectives, wherein at least one set of competing objectives is based on a delivery time criteria, and or fractionation criteria.

In one implementation, the criteria for the first type of radiation therapy treatment can include constraints and objective values for a photon therapy treatment plan. The parameter values can include dosage values, treatment time values, fractionation schedule values, toxicity probability values, motion management strategy, and the like. The criteria for the second type of radiation therapy treatment can include constraints and objectives for a proton therapy treatment plan. The criteria can include dosage, treatment time, fractionation schedule, toxicity probability, motion management, and the like.

In one implementation, parameter values of criteria for a photon therapy treatment plan can be imported and used as limiting optimization criteria to determine an optimized proton therapy treatment plan. In one implementation, maximum, minimum, average or the like parameter values such as dose levels to organs-at-risk can be converted to normal tissue complication probabilities which potentially give physicians better control over the quality versus time, fractionation, cost and the like tradeoffs.

At 930, one or more radiation therapy plans based on a multi-criteria optimization can be determined based on the criteria for the second type of radiation therapy treatment and constrained by the criteria parameter values for the first type of radiation therapy. In one implementation, the computing device 130 can be configured to perform a multi-criteria optimization based on the plurality of received criteria. For example, a solution set of Pareto optimal plans can be created, wherein the unique combinations of dose and delivery time can be explored. The values, priorities and the like of the competing objectives can be varied in addition to the dose-based objectives in order to create multiple candidate plans and to adequately sample the available space between different tradeoffs.

At 940, the one or more radiation therapy plans determined based on the multi-criteria optimization can be displayed. In one implementation, the one or more radiation therapy plans can be output on a display 165 by the computing device 130. The one or more radiation therapy plans can be displayed in one or more Graphical User Interfaces (GUIs) to one or more decision makers. In addition, the one or more radiation therapy plans can be stored in one or more computing device accessible data structures in the memory 145 of the computing device, in network attached storage, in cloud storage, or the like.

In one implementation, a ratio of the proton fractionation to the photon fractionation can be calculated. The proton to photon fractionation ratio can be displayed. A ratio of 0.5, for example, indicates that the proton treatment that is expected to be of equivalent quality in terms of local control and toxicity can be delivered with half the number of fractions as compared to the photon treatment.

The processes at 920-940 can be iteratively repeated any number of times. The planner is therefore, presented with the tools to compare the plans for dose coverage and treatment time, and estimate results base on the plans for other possible sets of radiation therapy treatment criteria. The processes at 920-940 can be repeated to determine a radiation therapy plan in each iterative cycle. In other implementations, multiple radiation therapy plans can be determined in each iterative cycle. Subsequent iterative cycles can also be used to determine new plans based on variations in treatment plans determined in previous cycles or linear combinations of multiple treatment plans determined in previous cycles.

In one implementation, an estimate of the delivery time and or fractionation schedule can be computed for each candidate plan. The delivery time and or fractionation schedule can then be used as an additional quality metric, which together with a set of selected dose-related quality metrics can define the position of the plan in the multi-dimensional tradeoff space. Based on the computed quality metric values, the iterative multi-criteria optimization can be performed. In the iterative phase, the user can have control of each selected quality metric, including the treatment time and or fractionation, and can therefore quickly explore Pareto optimal tradeoffs between the metrics.

In one example, proton therapy is typically more expensive per fraction than photon therapy. Insurance companies may be reluctant to pay more per fraction for dosimetric quality improvements. The tool in accordance with aspects of the present technology allows planners to create proton plans that can be equivalent in quality to best in class photon treatment plans, but that can be administer in fewer fractions effectively reducing the cost and time of the treatment. The plans can be prepared by a skilled planner and the comparison and decision can be taken by the doctor, allowing the doctor to examine several factors at once. For example, a toxicity, short-term or long-term, for a photon plan can be fixed at an acceptable percentage, the proton dose-to-target can then be escalated until the proton normal tissue complication probability matches the comparative photon plan. This can allow the clinician to escalate fractioned proton dose while holding toxicity to the comparative photon plan.

At 950, a selection of one or more of the determined radiation therapy plans can be received. In one implementation, the computing device 130 can receive a selection of a given radiation therapy plan of the second type from a member of the radiation oncology team. At 960, parameter values of the plurality of criteria of the one or more selected second type of radiation therapy plans can be output. In one implementation, the computing device 130 can output the parameter values of the selected radiation therapy plans for storage in a computing device executable data structure. In another implementation, the parameter values of the selected radiation therapy plan can be output to the radiation therapy treatment device 105-125 for controlling operation thereof.

In additional embodiments, the above described aspects of the present technology can be applied to a plurality of patients to explore system clinical capabilities. The optimized treatment plan for the plurality of patients can be used to determine, for example, if the treatment plan can achieve a set of clinical dose distribution objects in less than a specified amount of time. The clinical capability can be useful for system commissioning, in analyzing the tradeoffs of the dosimetric choices in the commissioning, marketing and or sale, analyzing clinical benefits of individual design changes during product development, and the like.

The foregoing descriptions of specific embodiments of the present technology have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. A radiation therapy treatment planning method comprising:
   receiving a plurality of criteria for a radiation therapy treatment, wherein the plurality of criteria includes one or more sets of competing objectives and wherein at least one set of competing objectives is based on a time criteria;
   determining one or more radiation therapy plans based on a multi-criteria optimization of the plurality of criteria for the radiation therapy treatment as a function of a dose quality at target, a dose quality for organs-at-risk and a delivery time; and
   displaying the one or more radiation therapy plans.

2. The method according to claim 1, wherein the time criteria comprises a delivery time criteria or fractionation criteria.

3. The method according to claim 1, wherein the plurality of criteria further includes one or more from a group consisting of a treatment modality criteria, a toxicity criteria, a cost criteria, and a motion management criteria.

4. The method according to claim 1, further comprising:
   receiving a revised one or more of the plurality of criteria of the radiation therapy treatment;

determining one or more revised radiation therapy plans based on the multi-criteria optimization of the revised one or more of the plurality of criteria for the radiation therapy treatment; and displaying the one or more revised radiation therapy plans.

5. The method according to claim 1, further comprising:
receiving a selection of one of the one or more radiation therapy plans; and
outputting parameter values for the plurality of criteria of the selected radiation therapy plan.

6. The method according to claim 1, further comprising:
receiving a plurality of criteria parameter values for a first type of radiation therapy treatment;
receiving the plurality of criteria for the radiation therapy treatment of a second type; and
determining the one or more radiation therapy plans for the second type based on the multi-criteria optimization of the plurality of criteria for the second type of radiation therapy treatment constrained by the plurality of criteria parameter values for the first type of radiation therapy treatment.

7. The method according to claim 6, wherein:
the first type of radiation therapy treatment comprises a photon therapy treatment; and
the second type of radiation therapy treatment comprises a proton therapy treatment.

8. A radiation therapy planning system comprising:
a display unit;
a storage unit; and
a host unit configured to:
   receive a plurality of criteria of a radiation therapy treatment, wherein the plurality of criteria includes one or more set of competing objects and wherein at least one set of competing objectives is based on a delivery time criteria or a fractionation criteria;
   determine one or more Pareto optimal radiation therapy plans based on a multi-criteria optimization of the plurality of criteria for the radiation therapy treatment optimized for at least one of the delivery time criteria or the fractionation criteria as a function of a dose quality at target, a dose quality for organs-at-risk and a delivery time; and
   display the one or more Pareto optimal radiation therapy plans.

9. The radiation therapy planning system of claim 8, wherein the plurality of criteria further includes one or more from a group consisting of a treatment modality criteria, a toxicity criteria, a cost criteria, and a motion management criteria.

10. The radiation therapy planning system of claim 8, wherein the host unit is further configured to:
receive a revised one or more of the plurality of criteria of the radiation therapy treatment;
determine one or more revised Pareto optimal radiation therapy plans based on the multi-criteria optimization of the revised one or more of the plurality of criteria for the radiation therapy treatment; and
display the one or more revised Pareto optimal radiation therapy plans.

11. The radiation therapy planning system of claim 8, wherein the host unit is further configured to:
receive a plurality of criteria parameter values for a first type of radiation therapy treatment;
receive the plurality of criteria for the radiation treatment plan of a second type; and
determining the one or more Pareto optimal radiation therapy plans for the second type based on the multi-criteria optimization of the plurality of criteria for the second type of radiation therapy treatment constrained by the plurality of criteria parameter values for the first type of radiation therapy treatment.

12. The radiation therapy planning system of claim 11, wherein
the first type of radiation therapy treatment comprises a photon therapy treatment; and
the second type of radiation therapy treatment comprises a proton therapy treatment.

13. One or more non-transitory computing device-readable storage mediums storing instructions executable by one or more computing devices to perform a radiation therapy treatment planning method comprising:
receiving a plurality of criteria for a radiation therapy treatment, wherein the plurality of criteria includes one or more sets of competing objectives and wherein at least one set of competing objectives is based on one or more of a delivery time or a fractionation schedule;
determining one or more radiation therapy plans based on a multi-criteria optimization of the plurality of criteria including the delivery time or fractionation schedule based set of competing objectives as a function of a dose quality at target, a dose quality for organs-at-risk and a delivery time; and
displaying the one or more radiation therapy plans.

14. The one or more non-transitory computing device-readable storage mediums storing instructions executable by one or more computing devices to perform a radiation therapy treatment planning method according to claim 13, further comprising:
receiving a revised one or more of the plurality of criteria of the radiation therapy treatment;
determining one or more revised radiation therapy plans based on the multi-criteria optimization of the revised one or more of the plurality of criteria for the radiation therapy treatment; and
displaying the one or more revised radiation therapy plans.

15. The one or more non-transitory computing device-readable storage mediums storing instructions executable by one or more computing devices to perform a radiation therapy treatment planning method according to claim 13, further comprising:
receiving a selection of one of the one or more radiation therapy plans; and
outputting parameter values for the plurality of criteria of the selected radiation therapy plan.

16. The one or more non-transitory computing device-readable storage mediums storing instructions executable by one or more computing devices to perform a radiation therapy treatment planning method according to claim 13, further comprising:
receiving a plurality of criteria parameter values for a first type of radiation therapy treatment;
receiving the plurality of criteria for the radiation treatment plan of a second type; and
determining the one or more radiation therapy plans for the second type based on the multi-criteria optimization of the plurality of criteria for the second type of radiation therapy treatment constrained by the plurality of criteria parameter values for the first type of radiation therapy treatment.

17. The one or more non-transitory computing device-readable storage mediums storing instructions executable by one or more computing devices to perform a radiation therapy treatment planning method according to claim 16, wherein:
    the first type of radiation therapy treatment comprises a photon therapy treatment; and
    the second type of radiation therapy treatment comprises a proton therapy treatment.

18. The one or more non-transitory computing device-readable storage mediums storing instructions executable by one or more computing devices to perform a radiation therapy treatment planning method according to claim 13, further comprising computing a ratio of a fractionation for the photon therapy treatment and a fractionation for the proton therapy treatment.

19. The method according to claim 6, further comprising:
    calculating a ratio of fractionation for the proton therapy treatment to fractionation for the proton therapy treatment; and
    outputting the ratio of fractionation for the proton therapy treatment to fractionation for the proton therapy treatment.

20. The radiation therapy planning system of claim 12, further comprising:
    calculating a ratio of fractionation for the second type of radiation therapy treatment to fractionation for the first type of radiation therapy; and
    outputting the ratio of fractionation for the second type of radiation therapy treatment to fractionation for the first type of radiation therapy.

\* \* \* \* \*